US008321035B2

(12) United States Patent
Koop

(10) Patent No.: US 8,321,035 B2
(45) Date of Patent: Nov. 27, 2012

(54) LAYERED ELECTRODE FOR AN IMPLANTABLE MEDICAL DEVICE LEAD

(75) Inventor: Brendan E. Koop, Ham Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 34 days.

(21) Appl. No.: 13/160,045

(22) Filed: Jun. 14, 2011

(65) Prior Publication Data

US 2012/0046721 A1 Feb. 23, 2012

Related U.S. Application Data

(60) Provisional application No. 61/374,709, filed on Aug. 18, 2010.

(51) Int. Cl.
*A61N 1/00* (2006.01)
(52) U.S. Cl. ....................................................... 607/116
(58) Field of Classification Search .................. 607/116; 600/378
See application file for complete search history.

(56) References Cited

U.S. PATENT DOCUMENTS

2004/0059402 A1\* 3/2004 Soukup et al. ................. 607/116
2007/0197892 A1\* 8/2007 Shen et al. ..................... 600/378

FOREIGN PATENT DOCUMENTS

EP 1985579 A2 10/2008
WO WO2008011721 A1 1/2008

OTHER PUBLICATIONS

International Search Report and Written Opinion issued in PCT/US2011/040345, mailed Oct. 28, 2011, 11 pages.

\* cited by examiner

*Primary Examiner* — George Manuel
*Assistant Examiner* — Robert N Wieland
(74) *Attorney, Agent, or Firm* — Faegre Baker Daniels LLP

(57) ABSTRACT

A medical device lead includes an insulative lead body, a conductor extending through the lead body from a proximal end to a distal end, and an electrode electrically connected to the conductor. The proximal end is adapted to be electrically connected to a pulse generator. The electrode includes a plurality of electrode modules mechanically coupled in a stack of electrode modules. Each electrode module includes a plurality of layers that define substantially similar sized pores such that the stack of electrode modules includes an array of the substantially similar sized pores.

20 Claims, 7 Drawing Sheets

LAYERED ELECTRODE FOR AN IMPLANTABLE MEDICAL DEVICE LEAD

CROSS-REFERENCE TO RELATED APPLICATION(S)

This application claims priority to Provisional Application No. 61/374,709, filed Aug. 18, 2010, which is herein incorporated by reference in its entirety.

TECHNICAL FIELD

The present invention relates to implantable medical devices. More particularly, the present invention relates to layered medical device lead electrodes formed from a plurality of electrode modules with similarly sized pores.

BACKGROUND

Cardiac pacing leads are well known and widely employed for carrying pulse stimulation signals to the heart from a battery operated pacemaker, or other pulse generating means, as well as for monitoring electrical activity of the heart from a location outside of the body. Electrodes are also used to stimulate the heart in an effort to mitigate bradycardia or terminate tachycardia or other arrhythmias. In all of these applications, it is highly desirable to optimize electrical performance characteristics of the electrode/tissue interface. Such characteristics include minimizing the threshold voltage necessary to depolarize adjacent cells, maximizing the electrical pacing impedance to prolong battery life, and minimizing sensing impedance to detect intrinsic signals.

Pacing (or stimulation) threshold is a measurement of the electrical energy required for a pulse to initiate a cardiac depolarization. The pacing threshold may rise after the development of a fibrous capsule around the electrode tip, which occurs over a period of time after implantation. The thickness of the fibrous capsule is generally dependent upon the mechanical characteristics of the distal end of the lead (i.e., stiff or flexible), the geometry of the electrode tip, the microstructure of the electrode tip, and the biocompatibility of the electrode and other device materials. In addition, the constant beating of the heart can cause the electrode to pound and rub against the surrounding tissue, causing irritation and a subsequent inflammatory response, eventually resulting in a larger fibrotic tissue capsule.

In a pacemaker electrode, minimal tissue reaction is desired around the tip, but firm intimate attachment of the electrode to the tissue is essential to minimize any electrode movement. A porous electrode tip with a tissue entrapping structure allows rapid fibrous tissue growth into a hollow area or cavity in the electrode tip to facilitate and enhance attachment of the electrode to the heart and increase biocompatibility. A reduced electrode dislodgement rate is also expected as a result of such tissue in-growth. A further aspect is selection of the average pore size, which must accommodate economical construction techniques, overall dimensional tolerances, and tissue response constraints. Tissue in-growth may assist in anchoring the electrode in place and increasing the contact surface area between the electrode and the tissue.

SUMMARY

Discussed herein are electrodes including a plurality of electrode modules mechanically coupled in a stack of electrode modules that includes an array of substantially similar sized pores, as well as medical electrical leads including such electrodes.

In Example 1, a medical device lead comprises an insulative lead body, a conductor extending through the lead body from a proximal end to a distal end, and an electrode electrically connected to the conductor. The proximal end is adapted to be electrically connected to a pulse generator. The electrode includes a plurality of electrode modules mechanically coupled in a stack of electrode modules. Each electrode module includes a plurality of layers that define substantially similar sized pores such that the stack of electrode modules includes an array of the substantially similar sized pores.

In Example 2, the medical device lead according to Example 1, wherein each electrode module comprises a plurality of electrode submodules that are mechanically secured together.

In Example 3, the medical device lead according to either Example 1 or 2, wherein at least two of the electrode submodules in each electrode module are hingedly attached.

In Example 4, the medical device lead according to any of Examples 1-3, wherein each of the plurality of electrode modules comprises coupling features that cooperate with coupling features on adjacent electrode modules in the stack of electrode modules to mechanically secure the plurality of electrode modules together.

In Example 5, the medical device lead according to any of Examples 1-4, wherein the coupling features on adjacent electrode modules cooperate in a snap-fit relationship.

In Example 6, the medical device lead according to any of Examples 1-5, wherein the plurality of electrode modules are welded together.

In Example 7, the medical device lead according to any of Examples 1-6, wherein each of the electrode modules are annular, and wherein the stack of electrode modules forms a ring electrode.

In Example 8, the medical device lead according to any of Examples 1-7, wherein the pores have widths in the range about 30 µm to about 60 µm In Example 9, an implantable electrode for a medical device lead comprises a plurality of electrode modules mechanically coupled in a stack of electrode modules. Each electrode module includes a plurality of layers that define substantially similar sized pores such that the stack of electrode modules includes an array of the substantially similar sized pores.

In Example 10, the implantable electrode according to Example 9, wherein each electrode module comprises a plurality of electrode submodules that are mechanically secured together.

In Example 11, the implantable electrode according to either Example 9 or 10, wherein at least two of the electrode submodules in each electrode module are hingedly attached.

In Example 12, the implantable electrode according to any of Examples 9-11, wherein each of the plurality of electrode modules comprises coupling features that cooperate with coupling features on adjacent electrode modules in the stack of electrode modules to mechanically secure the plurality of electrode modules together.

In Example 13, the implantable electrode according to any of Examples 9-12, wherein the coupling features on adjacent electrode modules cooperate in a snap-fit relationship.

In Example 14, the implantable electrode according to any of Examples 9-13, wherein the plurality of electrode modules are welded together.

In Example 15, the implantable electrode according to any of Examples 9-14, wherein each of the electrode modules is annular, and wherein the stack of electrode modules forms a ring electrode.

In Example 16, the implantable electrode according to any of Examples 9-15, wherein the pores have widths in the range about 30 µm to about 40 µm In Example 17, a method for forming an electrode for a medical device lead includes forming a plurality of electrode submodules each including a plurality of layers that define substantially similar sized pores and coupling features. A plurality of electrode modules are assembled from the electrode submodules by mechanically securing the electrode submodules together. The plurality of electrode modules are coupled together to form a stack of electrode modules. The coupling features of adjacent electrode modules in the stack of electrode modules cooperate to mechanically secure the electrode modules together. The stack of electrode modules includes an array of the substantially similar sized pores.

In Example 18, the method according to Example 17, wherein the coupling step comprises snapping the plurality of electrode modules together.

In Example 19, the method according to either Example 17 or 18, wherein the assembling step comprises hingedly attaching at least two of the electrode submodules together.

In Example 20, the method according to any of Examples 17-19, wherein the forming step comprises depositing successive alternating layers of a patterned sacrificial metal and an electrode metal on a substrate, etching the patterned sacrificial metal from the plurality of electrode submodules, and singulating the plurality of electrode submodules.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
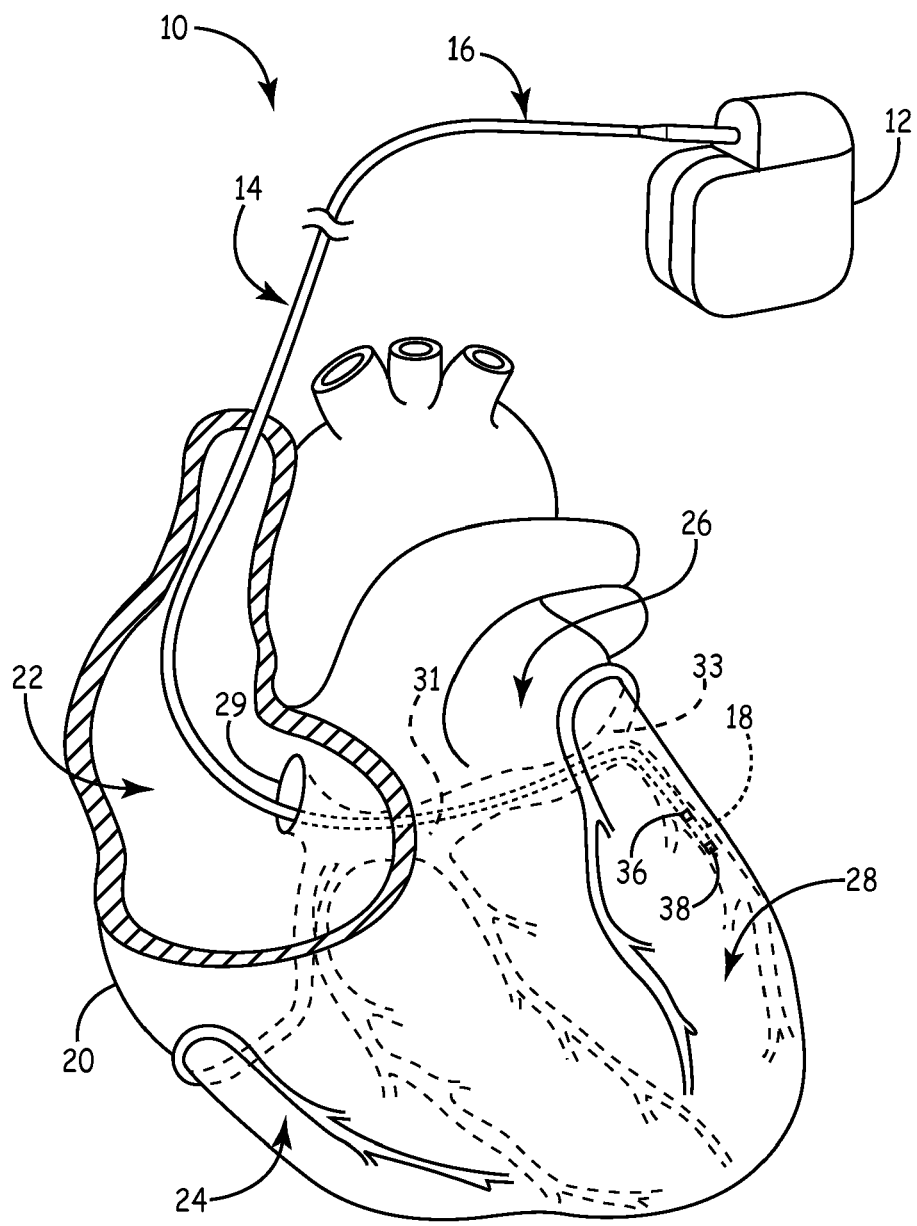
FIG. 1 is a schematic drawing of a cardiac rhythm management system including a pulse generator coupled to a lead including porous electrodes deployed in a patient's heart.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of a cardiac rhythm management system 10 including an implantable medical device (IMD) 12 with a lead 14 having a proximal end 16 and a distal end 18. In one embodiment, the IMD 12 includes a pulse generator. The IMD 12 can be implanted subcutaneously within the body, typically at a location such as in the patient's chest or abdomen, although other implantation locations are possible. The proximal end 16 of the lead 14 can be coupled to or formed integrally with the IMD 12. The distal end 18 of the lead 14, in turn, can be implanted at a desired location in or near the heart 20.

As shown in FIG. 1, distal portions of lead 14 are disposed in a patient's heart 20, which includes a right atrium 22, a right ventricle 24, a left atrium 26, and a left ventricle 28. In the embodiment illustrated in FIG. 1, the distal end 18 of the lead 14 is transvenously guided through the right atrium 22, through the coronary sinus ostium 29, and into a branch of the coronary sinus 31 or the great cardiac vein 33. The illustrated position of the lead 14 can be used for sensing or for delivering pacing and/or defibrillation energy to the left side of the heart 20, or to treat arrhythmias or other cardiac disorders requiring therapy delivered to the left side of the heart 20. Additionally, it will be appreciated that the lead 14 can also be used to provide treatment in other regions of the heart 20 (e.g., the right ventricle 24).

Although the illustrative embodiment depicts only a single implanted lead 14, it should be understood that multiple leads can be utilized so as to electrically stimulate other areas of the heart 20. In some embodiments, for example, the distal end of a second lead (not shown) may be implanted in the right atrium 22, and/or the distal end of a third lead (not shown) may be implanted in the right ventricle 24. Other types of leads such as epicardial leads may also be utilized in addition to, or in lieu of, the lead 14 depicted in FIG. 1.

During operation, the lead 14 can be configured to convey electrical signals between the IMD 12 and the heart 20. For example, in those embodiments where the IMD 12 is a pacemaker, the lead 14 can be utilized to deliver electrical stimuli for pacing the heart 20. In those embodiments where the IMD 12 is an implantable cardiac defibrillator, the lead 14 can be utilized to deliver electric shocks to the heart 20 in response to an event such as a heart attack or arrhythmia. In some embodiments, the IMD 12 includes both pacing and defibrillation capabilities.

In the embodiment shown, the lead 14 includes ring electrode 36 and tip electrode 38 at distal end 18. The ring electrode 36 and the tip electrode 38 are connected to one or more conductors that extend through the lead body from the IMD 12 to the distal end 18. The ring electrode 36 and/or the tip electrode 38 may be configured to deliver therapeutic electrical signals generated by the IMD 12 to adjacent tissue in the heart 20. The ring electrode 36 and/or the tip electrode 38 may also be configured to sense activity in the heart 20, and provide electrical signals related to the sensed activity to the IMD 12.

According to the present invention, the ring electrode 36 and/or tip electrode 38 include a plurality of pores formed in the conductive electrode material that have substantially similar dimensions. The porous electrodes 36 and/or 38 promote tissue growth into the pores, thereby coupling the lead 14 to the adjacent tissue. In addition, the pores are sized to minimize the collagen capsule thickness of the ingrown tissue, thus minimizing the pacing threshold voltage needed to depolarize the tissue. In some embodiments, the pores have widths in the range of about 30 µm to about 60 µm. The width refers to an average distance between two points across a pore.

Figure 2:
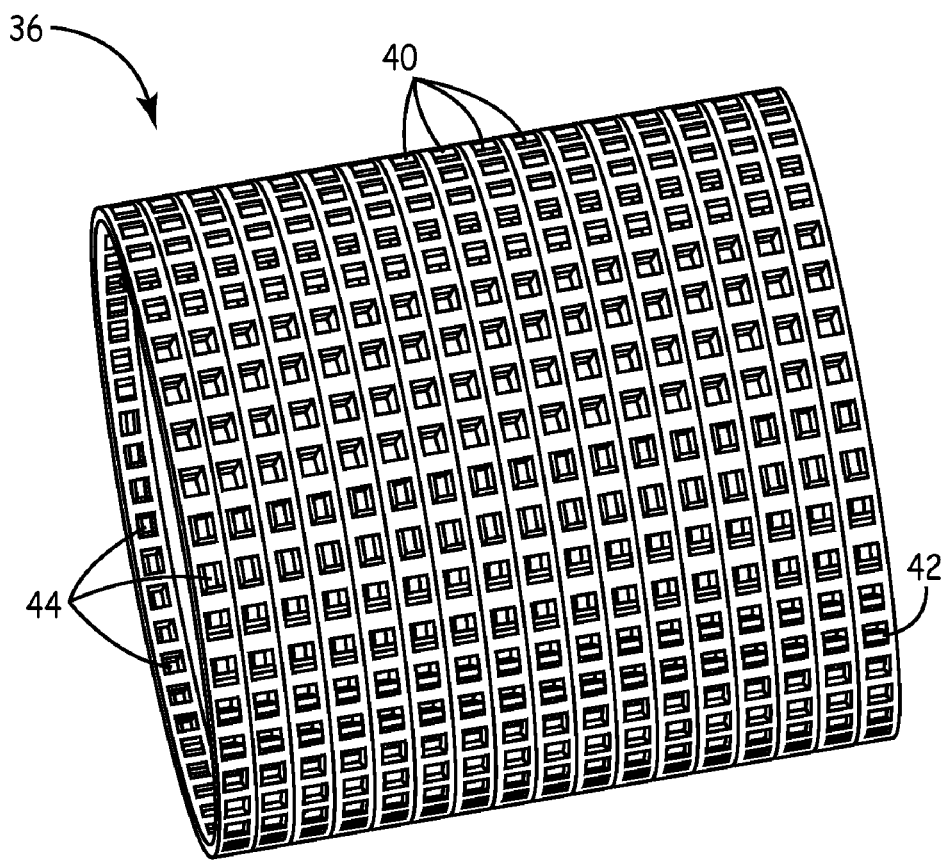
FIG. 2 is a perspective view of an exemplary embodiment of an electrode suitable for use in the cardiac rhythm management system shown in FIG. 1.

FIG. 2 is a perspective view of a ring electrode 36 according to an embodiment of the present invention. While the following description relates to embodiments of the ring electrode 36, the principles and processes described are adaptable to fabricate other types of electrodes and structures on the lead 14, such as the tip electrode 38. The ring electrode 36 includes a plurality of electrode modules 40 mechanically coupled in a stack 42 of electrode modules 40, as explained in further detail below. Each electrode module 40 includes a plurality of pores 44. Thus, when the electrode modules 40 are assembled into the stack 42, the stack 42 includes an array of pores 44. In an alternative embodiment, the ring electrode 36 is a single, continuous element that defines an array of pores 44.

Figure 3A:
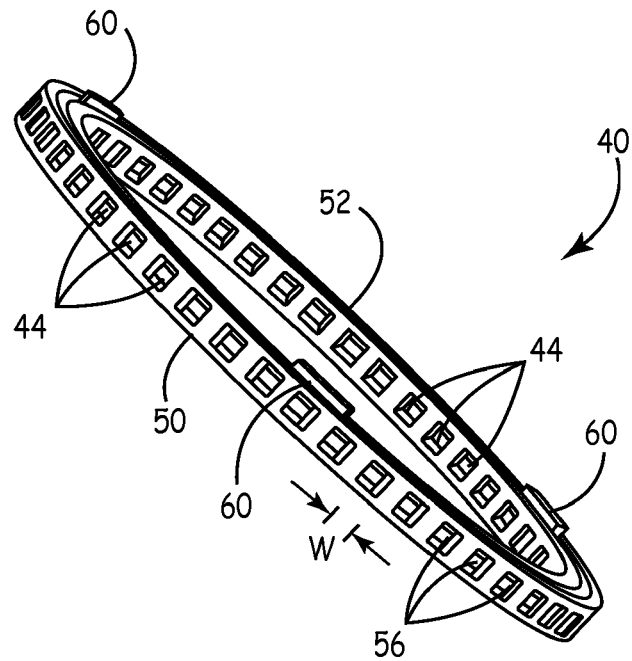
FIGS. 3A and 3B are perspective views of an electrode module that is connectable with similar electrode modules to form the electrode shown in FIG. 2.
Figure 3B:
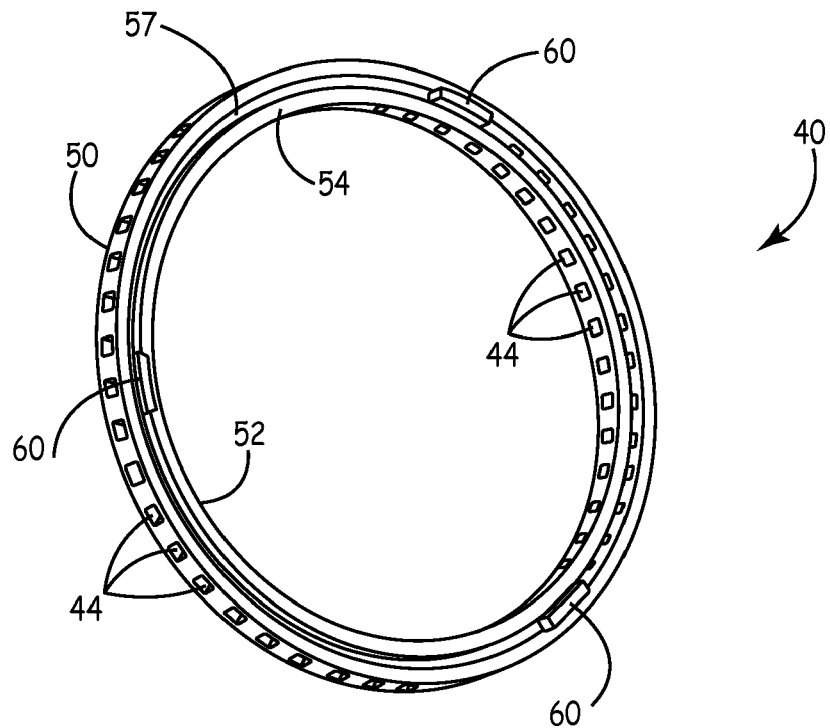

FIG. 3A is a side perspective view and FIG. 3B is a top perspective view of an electrode module 40 according to an embodiment of the present invention. In the embodiment shown, the electrode module 40 includes an outer ring 50 and inner ring 52 connected by an intermediate ring 54. The outer ring 50 and inner ring 52 each includes a plurality of pores 44 around its circumference. The intermediate ring 54 couples the outer ring 50 and inner ring 52 at posts 56 that extend between the pores 44. The height of the intermediate ring 54 is less than the height of the outer ring 50 and inner ring 52 such that the intermediate ring 54 defines a slot 57 extending between the outer ring 50 and inner ring 52. The electrode module 40 may include a slot 56 on the top and bottom of the rings 50, 52. While the electrode module 40 is shown including rings 50, 52, and 54, the electrode module 40 can have other configurations, such as a single porous ring.

The electrode module 40 may be comprised of a material suitable for an implantable medical device lead electrode, such as palladium (Pd), platinum (Pt), platinum-iridium (PtIr), titanium (Ti), nickel-titanium (NiTi), tantalum (Ta), MP35N alloy, or stainless steel.

The pores 44 have a generally square or rectangular shape in the embodiment shown, but other shapes are also possible (e.g., circular). Each electrode pore 44 has a width w, measured between adjacent posts 56 of the outer ring 50 or inner ring 52. In some embodiments, the widths w of the electrode pores 44 are within about 20% of the mean width of the electrode pores 44.

The electrode 36 including electrode pores 44 promotes tissue in-growth to secure the lead 14 relative to the adjacent tissue of the heart 20, thereby lowering the likelihood of dislodgement of the lead 14. In addition, the electrode pores 44 are sized substantially similar with dimensions to minimize the thickness of collagen capsules of ingrown tissue. Collagen capsules with reduced thickness allow a lower voltage to be used to depolarize surrounding myocardial tissue. A minimum thickness of fibrous encapsulation occurs when the width of the electrode pores 44 is about 35 µm to about 40 µm. Thus, in some embodiments, the width w of the electrode pores 44 is in the range of about 30 µm to about 60 µm.

The intermediate ring 54 includes a plurality of coupling features 60 that extend above a top surface of the outer ring 50 and inner ring 52. When the electrode modules 40 are assembled into the stack 42 of electrode modules 40 shown in FIG. 2, the coupling features 60 are configured to cooperate with a coupling feature on an adjacent electrode module 40 in the stack 42. For example, the coupling features 60 may slide into the slot 56 on the bottom of an adjacent electrode module 40 in the stack 42. The coupling features 60 may also be configured to couple with an adjacent electrode module 40 in the stack 42 via a snap-fit relationship. The electrode modules 40 may additionally or alternatively be welded to each other when they are assembled into the stack 42 to secure the electrode modules 40 together.

In some embodiments, the electrode modules 40 are fabricated using a layered deposition process. This allows for the fabrication of complex, micro-scale features with very tight tolerances (e.g., ±2 µm). In addition, the thickness of the electrode wall can be made very small (e.g., ~100 µm), which improves the electrical response of the electrode. In some embodiments, the electrode modules are formed by depositing successive alternating layers of a patterned sacrificial metal and an electrode metal on a substrate, etching the patterned sacrificial metal from the plurality of electrode modules, and singulating the plurality of electrode modules. After singulation, the electrode modules 40 may be assembled into the stack 42. An example of this process is described below with regard to FIGS. 4, 5, and 6A-6E.

Figure 4:
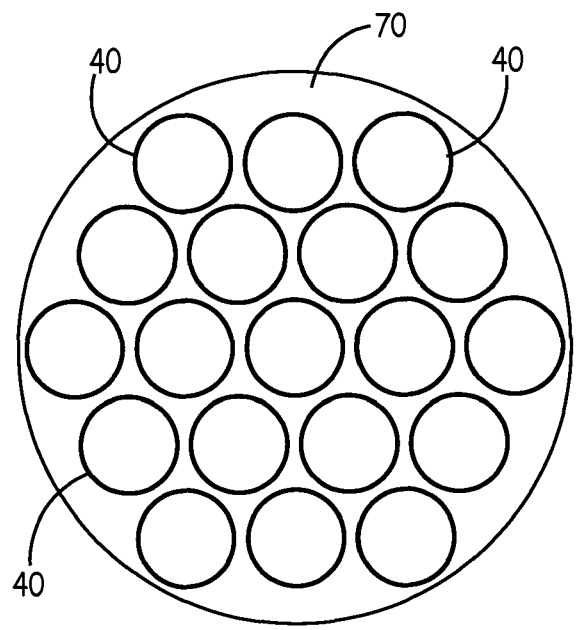
FIG. 4 is a plan view of a plurality of electrode modules formed on a substrate.

FIG. 4 is a plan view of a plurality of electrode modules 40 formed on a substrate 70, such as a silicone wafer or other semiconductor substrate. The electrode modules 40 are formed by patterning layers onto the substrate 70 in the desired shape. The electrode modules 40 are arranged on the substrate 70 to maximize the number of electrode modules 40 formed on the substrate 70. The size of the electrode modules 40 is exaggerated for purposes of illustration, but in actual implementation, many more electrode modules 40 may be formed on the substrate 70 due to the relative sizes of the electrode modules 40 and substrate 70.

Figure 5:
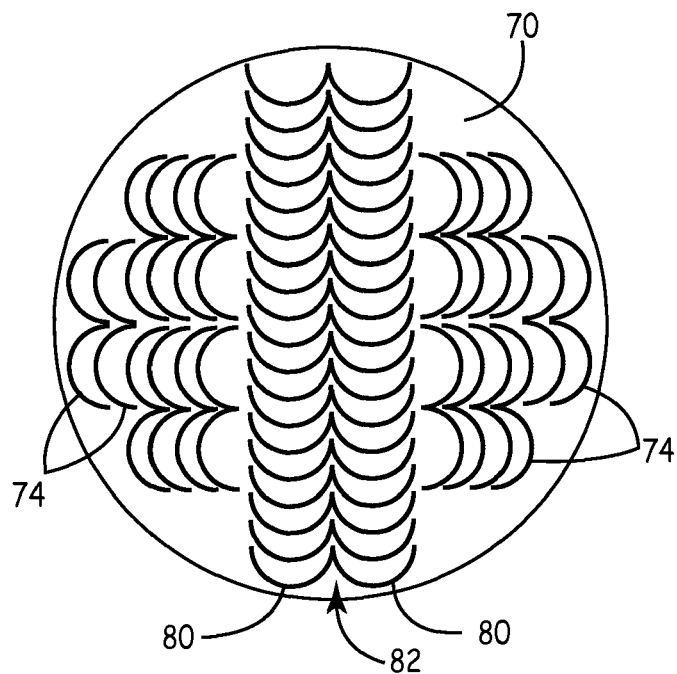
FIG. 5 is a plan view of a plurality of electrode submodules that are connectable to form electrode modules.

FIG. 5 is a plan view of a plurality of electrode submodules 74 formed on a substrate 70 according to an alternative embodiment. In this embodiment, the number of components that can be formed on the substrate 70 is increased, as compared to the embodiment shown in FIG. 4. The electrode submodules 74 include two semi-annular elements 80 connected by a hinge 82. After singulation, the hinge 82 is configured to allow the semi-annular elements 80 to rotate about the hinge 82 to bring the ends of the semi-annular elements 80 opposite the hinge 82 into contact with each other. When the ends are coupled together, the semi-annular elements 80 may be secured together (e.g., by welding or snap-fit) to form an electrode module 40. The semi-annular elements 80 may also include mechanical coupling features that facilitate coupling of the ends semi-annular elements 80 opposite the hinge 82. The size of the electrode submodules 74 is exaggerated for purposes of illustration, but in actual implementation, many more electrode submodules 74 may be formed on the substrate 70 due to the relative sizes of the electrode submodules 74 and substrate 70.

Alternative configurations for the electrode submodules 74 are also possible. For example, the semi-annular elements 80 shown may alternatively be formed separately (i.e., not connected by a hinge 82) and subsequently coupled with and secured to another semi-annular element 80. The electrode submodules 74 may also be fabricated as smaller or larger portions of the electrode modules 40 (e.g., quarter ring).

The electrode modules 40 (or electrode submodules 74) may also be formed in different sizes to generate an electrode having a different shape or configuration. For example, to form a tip electrode 38, the size of the electrode modules 40 may be controlled such that the stack 42 of electrode modules 40 is configured as the tip electrode 38. In addition, modules and submodules may also be formed on the substrate 70 that form other types of devices when assembled.

FIGS. 6A-6F illustrate steps in an exemplary process for forming the electrode modules 40 (or electrode submodules 74). FIGS. 6A-6F illustrate the formation of a single electrode module 40, but in actual implementation multiple electrode modules 40 or electrode submodules 74 may be formed on a substrate (e.g., substrate 70). Each of the layers of the electrode modules 40 may be comprised of a material suitable for an implantable medical device lead electrode, such as palladium (Pd), platinum (Pt), platinum-iridium (PtIr), titanium (Ti), nickel-titanium (NiTi), tantalum (Ta), MP35N alloy, or stainless steel.

In each of the steps described, a sacrificial layer may be deposited in a pattern that defines the contours of the portion of the electrode module 40 being formed. The sacrificial layer may be deposited using additive or subtractive deposition. For example, the sacrificial layer may be evaporated, sputtered, or plated. As another example, the sacrificial layer may also be deposited onto the substrate using powder metallurgy techniques. It is noted that the preceding examples should not be construed as limiting, and any suitable deposition technique may be used.

Figure 6A:
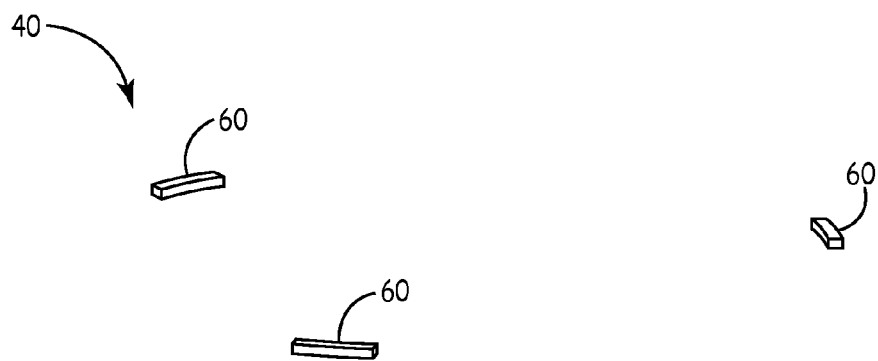
FIGS. 6A-6F are perspective views of an embodiment of a process for fabricating medical device lead electrodes modules.

In FIG. 6A, an electrode metal layer is deposited to form the coupling elements 60. For example, the coupling elements 60 may be formed onto a sacrificial layer defining the contours of the coupling elements 60. In some embodiments, the coupling elements 60 are deposited substantially uniformly over the sacrificial layer such that portions of the coupling elements 60 fill the spaces in the sacrificial layer and cover the patterned portions of the sacrificial layer. The coupling elements 60 may be deposited using any suitable deposition technique, such as those described with regard to the sacrificial layer. After the coupling elements 60 are formed, the metal layer at the top surface of the electrode module 40 is planarized until the sacrificial layer is exposed at the top surface through the electrode metal layer.

Figure 6B:
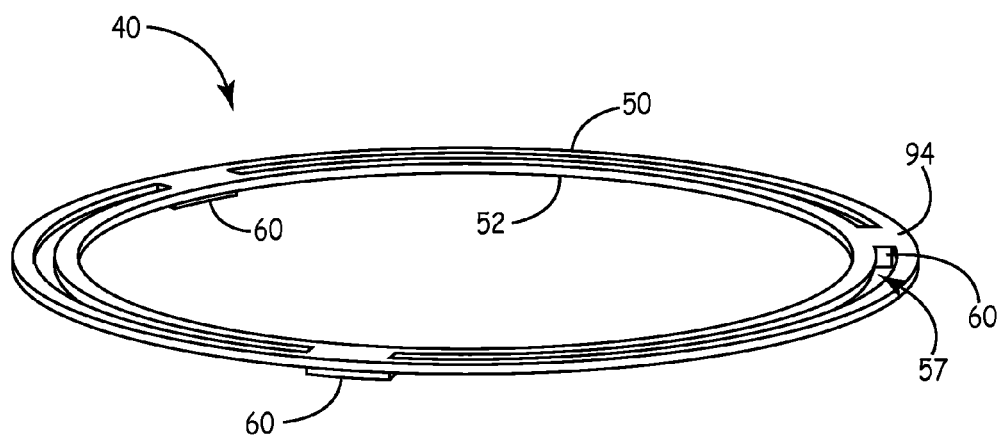

In FIG. 6B, a bottom structure 94 of the electrode module 40 is formed. The bottom structure 94 may be formed on a sacrificial layer that defines the contours of the bottom structure 94. The bottom structure 94 includes the first layer of the outer ring 50 and inner ring 52. The slot 57 extends between the outer ring 50 and inner ring 52. The slot 57 is discontinuous at the coupling elements 60. After the bottom structure 94 is formed, the metal layer at the top surface of the electrode module 40 is planarized until the sacrificial layer is exposed at the top surface through the electrode metal layer.

Figure 6C:
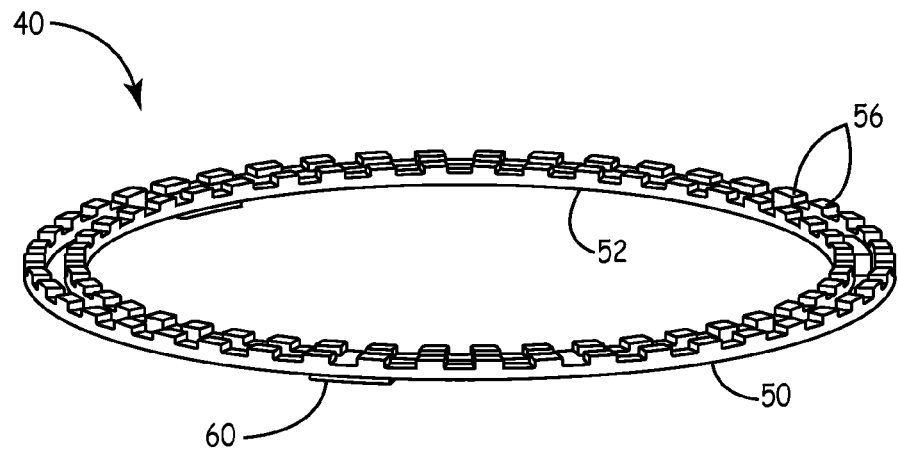

In FIG. 6C, a bottom portion of the posts 56 are formed on the bottom structure 94. The bottom portion of the posts 56 may be formed on a sacrificial layer that defines the contours of the bottom of the posts 56. After the bottom portion of the posts 56 is formed, the metal layer at the top surface of the electrode module 40 is planarized until the sacrificial layer is exposed at the top surface through the electrode metal layer.

Figure 6D:
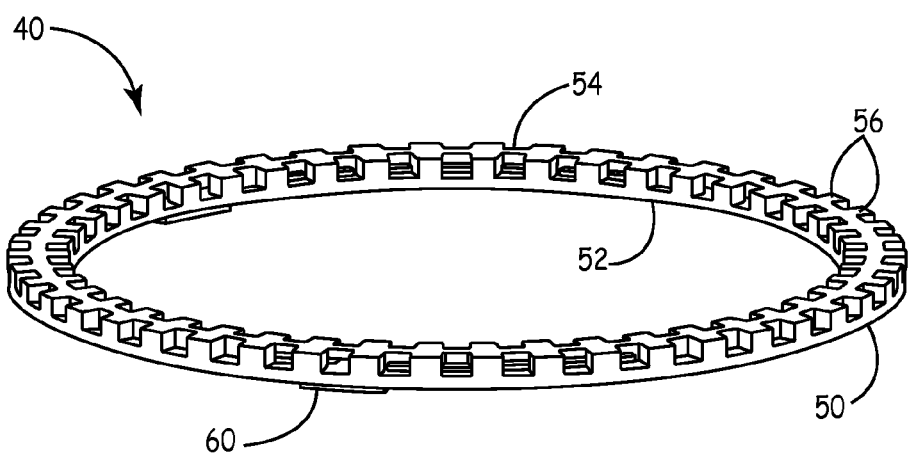

In FIG. 6D, a middle portion of the posts 56 and the intermediate ring 54 are formed on the bottom portion of the posts 56. The middle portion of the posts 56 and the intermediate ring 54 may be formed on a sacrificial layer that defines the contours of the middle portion of the posts 56 and the intermediate ring 54. After the middle portion of the posts 56 and the intermediate ring 54 are formed, the metal layer at the top surface of the electrode module 40 is planarized until the sacrificial layer is exposed at the top surface through the electrode metal layer.

Figure 6E:
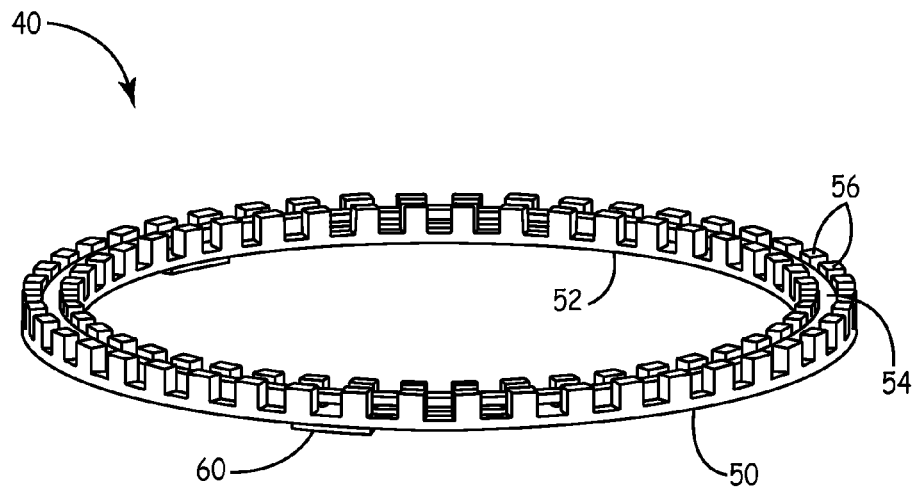

In FIG. 6E, a top portion of the posts 56 is formed on the middle portion of the posts 56. The top portion of the posts 56 may be formed on a sacrificial layer that defines the contours of the top portion of the posts 56. After the top portion of the posts 56 is formed, the metal layer at the top surface of the electrode module 40 is planarized until the sacrificial layer is exposed at the top surface through the electrode metal layer.

Figure 6F:
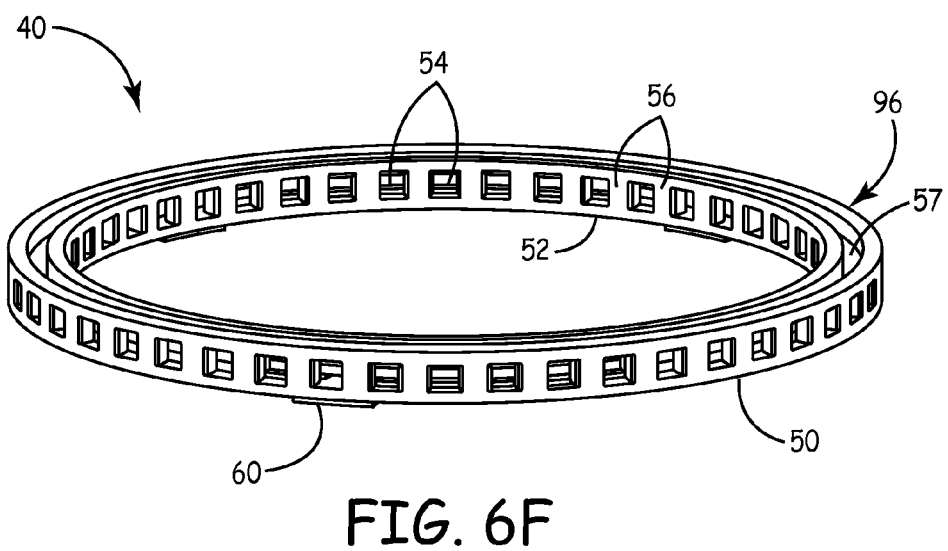

In FIG. 6F, a top structure 96 of the electrode module 40 is formed. The top structure 96 may be formed on a sacrificial layer that defines the contours of the top structure 96. The top structure 96 includes the second layer of the outer ring 50 and inner ring 52. The slot 57 extends between the outer ring 50 and inner ring 52. In some embodiments, the slot 57 is continuous along the top structure 96. In other embodiments, features are formed in the slot 57 that mate with the coupling elements 60. The bottom structure 94, posts 56, and top structure 96 define the pores 44 in the outer ring 50 and inner ring 52. After the top structure 96 is formed, the sacrificial layers are removed from the electrode module 40.

In summary, embodiments of the present invention relate to a medical device lead including an insulative lead body, a conductor extending through the lead body from a proximal end to a distal end, and an electrode electrically connected to the conductor. The proximal end is adapted to be electrically connected to a pulse generator. The electrode is electrically connected to the conductor and includes a plurality of electrode modules mechanically coupled in a stack of electrode modules. Each electrode module includes a plurality of layers that define substantially similar sized pores such that the stack of electrode modules includes an array of the substantially similar sized pores. The electrode pores may be sized to minimize the thickness of collagen capsules of ingrown tissue, which minimizes the threshold voltage of the ingrown tissue. In some embodiments, the pores have diameters in the range of about 30 µm to about 60 µm. In addition, the tissue in-growth secures the lead relative to the adjacent tissue, thereby lowering the likelihood of dislodgement of the cardiac lead.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

I claim:

1. A medical device lead comprising:
an insulative lead body;
a conductor extending through the lead body from a proximal end to a distal end, wherein the proximal end is adapted to be electrically connected to a pulse generator; and
an electrode electrically connected to the conductor, the electrode including a plurality of electrode modules mechanically coupled in a stack of electrode modules, each electrode module including a plurality of layers that define substantially similar sized pores such that the stack of electrode modules includes an array of the substantially similar sized pores.

2. The medical device lead of claim 1, wherein each electrode module comprises a plurality of electrode submodules that are mechanically secured together.

3. The medical device lead of claim 2, wherein at least two of the electrode submodules in each electrode module are hingedly attached.

4. The medical device lead of claim 1, wherein each of the plurality of electrode modules comprises coupling features that cooperate with coupling features on adjacent electrode modules in the stack of electrode modules to mechanically couple the plurality of electrode modules.

5. The medical device lead of claim 4, wherein the coupling features on adjacent electrode modules cooperate in a snap-fit relationship.

6. The medical device lead of claim 1, wherein the plurality of electrode modules are welded together.

7. The medical device lead of claim 1, wherein each of the electrode modules are annular, and wherein the stack of electrode modules forms a ring electrode.

8. The medical device lead of claim 1, wherein the pores have widths in the range about 30 μm to about 60 μm.

9. An implantable electrode for a medical device lead comprising a plurality of electrode modules mechanically coupled in a stack of electrode modules, each electrode module comprising a plurality of layers that define substantially similar sized pores such that the stack of electrode modules includes an array of the substantially similar sized pores.

10. The implantable electrode of claim 9, wherein each electrode module comprises a plurality of electrode submodules that are mechanically secured together.

11. The implantable electrode of claim 10, wherein at least two of the electrode submodules in each electrode module are hingedly attached.

12. The implantable electrode of claim 9, wherein each of the plurality of electrode modules comprises coupling features that cooperate with coupling features on adjacent electrode modules in the stack of electrode modules to mechanically couple the plurality of electrode modules.

13. The implantable electrode of claim 12, wherein the coupling features on adjacent electrode modules cooperate in a snap-fit relationship.

14. The implantable electrode of claim 9, wherein the plurality of electrode modules are welded together.

15. The implantable electrode of claim 9, wherein each of the electrode modules is annular, and wherein the stack of electrode modules forms a ring electrode.

16. The implantable electrode of claim 9, wherein the pores have widths in the range about 30 μm to about 60 μm.

17. A method for forming an electrode for a medical device lead, the method comprising:
    forming a plurality of electrode submodules each including a plurality of layers that define substantially similar sized pores and coupling features;
    assembling a plurality of electrode modules from the plurality of the electrode submodules by mechanically securing the plurality of electrode submodules together; and
    coupling the plurality of electrode modules together to form a stack of electrode modules, the coupling features of adjacent electrode modules in the stack of electrode modules cooperating to mechanically secure the electrode modules together, the stack of electrode modules forming an electrode body including an array of the substantially similar sized pores.

18. The method of claim 17, wherein the coupling step comprises:
    snapping the plurality of electrode modules together.

19. The method of claim 17, wherein the assembling step comprises:
    hingedly attaching at least two of the electrode submodules together.

20. The method of claim 17, wherein the forming step comprises:
    depositing successive alternating layers of a patterned sacrificial metal and an electrode metal on a substrate;
    etching the patterned sacrificial metal from the plurality of electrode submodules; and
    singulating the plurality of electrode submodules.

\* \* \* \* \*